United States Patent [19]
Iqbal

[11] 3,947,458
[45] Mar. 30, 1976

[54] PREPARATION OF AMINES

[75] Inventor: Abul F. M. Iqbal, Glattbrugg, Switzerland

[73] Assignee: Monsanto Company, St. Louis, Mo.

[22] Filed: Jan. 28, 1974

[21] Appl. No.: 437,408

Related U.S. Application Data

[63] Continuation of Ser. No. 207,629, Dec. 13, 1971, abandoned.

[30] Foreign Application Priority Data

Dec. 22, 1970 Switzerland............... 19166/70

[52] U.S. Cl...... 260/293.51; 260/326.8; 260/583 R; 260/563 R
[51] Int. Cl.² ..................... C07D 211/06
[58] Field of Search ........ 260/326.8, 583 R, 563 R, 260/293.51

[56] References Cited
UNITED STATES PATENTS

| | | | |
|---|---|---|---|
| 2,497,310 | 2/1950 | Larson | 260/585 |
| 3,513,200 | 5/1970 | Biale | 260/583 |
| 3,758,586 | 9/1973 | Coulson | 260/583 |

*Primary Examiner*—R. Gallagher
*Assistant Examiner*—James H. Turnipseed

[57] ABSTRACT

Amines are prepared by reacting ammonia, a primary amine or a secondary amine with an olefin, carbon monoxide and water in the presence of a rhodium catalyst which is rhodium oxide or a rhodium compound capable of forming a rhodium carbonyl and iron carbonyl.

5 Claims, No Drawings

PREPARATION OF AMINES

The present patent application is a continuation of Ser. No. 207,629 filed Dec. 13, 1971, and now abandoned.

BACKGROUND OF THE INVENTION

1. Field of the Invention

This invention relates to the preparation of amines. In a particular aspect, this invention relates to the preparation of amines by reacting ammonia, a primary amine or a secondary amine with an olefin, carbon monoxide and water. In a more particular aspect, this invention relates to the preparation of amines by carrying out the said reaction in the presence of catalyst which is (a) rhodium oxide or a rhodium compound capable of forming a rhodium carbonyl and (b) iron carbonyl.

2. Description of the Prior Art

The preparation of amines by reacting an olefin with ammonia, a primary amine or a secondary amine, carbon monoxide and water, in the presence of a metal carbonyl hydride at elevated temperatures and pressures is known (for example from German Patent No. 839,800 (May 5, 1952). It has also been known to replace the carbon monoxide by ammonium formiates (German Patent No. 909,937). It has further been known to use ammonia or amines in the form of salts of phosphoric acid, sulfuric acid or carboxylic acids having more than one carbon atom, in order to avoid formation of ammonium carbonate or amine carbonates which, owing to their volatility, evolve from the liquid reaction mixture and clog the reactor pipings, (See German Patent No. 931,948). Cumbersome separation and recycling steps are necessary when the above-described methods are employed in a continuous process.

Iron pentacarbonyl has been most widely employed as the catalyst in the above-referred-to procedures. Other catalysts such as cobalt, nickel, ruthenium, iron, and copper, their compounds and alloys, moreover, fused coppersilica, cobalt chromite, cobalt-substituted amines, cobalt salts of organic carboxylic acids, nickel carbonyl and cobalt carbonyl, have also been proposed as catalysts for the aminomethylation of olefins. Copper-containing substances have been stated to be among the most active catalysts (see U.S. Pat. No. 2,497,310).

It has further been known to use amino carboxylic acids, their esters, or salts, containing at least one hydrogen atom on the amino group, as an amine reactant in the aminomethylation of ethylene and propylene (British Patent No. 803,778, filed 22.11.1956, and issued 29.10.1958).

The aminomethylation reaction for the preparation of amines has also been catalyzed by metal carbonyls or metal carbonyl hydrides, particularly iron carbonyl hydride. In the work reported by W. Reppe et al illustrating the reaction, iron carbonyl and its hydride have been exclusively as catalysts. In contrast to the known Oxo synthesis or hydroformylation, rather large quantities of the toxic iron pentacarbonyl are required, a substantial portion of which is consumed because of a release of carbon monoxide and conversion to ionic divalent iron which precipitates in the presence of carbon dioxide in the form of catalytically inactive carbonates, and oxides. The iron carbonyl thus simultaneously acts as a source of carbon monoxide. When ammonia or amines are used as reactants, the carbon dioxide formed during the reaction has to be removed continuously from the reaction gases, in order to maintain an optimum carbon monoxide pressure and thus to minimize the loss of catalyst through carbonate formation. Prolonged reaction periods are necessary for somewhat satisfactory yields.

In the procedure referred to above, only the aminomethylation of ethylene and propylene has been reduced to actual practice. The overall yields of alkylated amines in general have not exceeded 50%, when calculated on the amount of ammonia or amine originally used in the reaction. Substantial quantities of by-products such as amine carbonates, amine formiates, heterocyclic amines, amides, alcohols, aldehydes, dimers and polymers of olefin, saturated hydrocarbons, iron carbonate, iron (II) oxide and iron (III) oxide, are commonly obtained by these previous methods.

It has been suggested also that higher olefins and cyclic olefins can be brought to reaction by the above-referred-to procedures. My attempts to extend the known iron carbonyl catalyzed synthesis to such olefinic substrates met with little success. My experimentation indicates that iron pentacarbonyl fails to catalyze to any essential extent the reaction with higher olefins.

It is also known that aminomethylation of $C_{10}$ to $C_{13}$ olefins can be performed with secondary alkyl amines in the presence of a cobalt carbonyl hydrocarbyl phosphine complex as catalyst. However, hydrogen has been used instead of water (U.S. Pat. No. 3,234,283). The yields of tertiary amines did not exceed 50%, based upon the olefin. Substantial quantities of the corresponding alcohol (oxo product), and also of formamide (from carbonylation of amine), aldehyde (intermediate) and saturated hydrocarbon (from hydrogenation of olefin) are indicated as having been formed as by-products.

SUMMARY OF THE INVENTION

It has now been discovered that rhodium oxide when used in accordance with the present invention exhibits far superior catalytic properties in the aminomethylation of olefins, using water as a source of hydrogen, when compared with iron pentacarbonyl. It has been further found in accordance with the present invention that iron pentacarbonyl displays a strong synergistic action upon rhodium oxide to increase the selectivity and yield of the desired amine. In accordance with the present invention, a highly active catalyst for the aminomethylation of olefins is formed by mixing iron pentacarbonyl with rhodium oxide. Substantially smaller quantities of iron carbonyl fit the process, when compared with the old procedures.

Iron carbonyl concentrations as low as e.g., 0.5–5 mol %, based upon olefin, can be employed with success, and very small amounts of rhodium oxide such as e.g., 0.01–0.5 mol %, based upon olefin, are sufficient for the herein disclosed aminomethylation procedure. The ratio of iron pentacarbonyl to rhodium compound is preferably in the range of from 10:1 and 100:1. This reduces to a great extent the hazards involved in handling large amounts of toxic iron carbonyl. These results are superior to those obtained with either iron pentacarbonyl or rhodium oxide individually.

DETAILED DESCRIPTION

The total amount of the organic base employed in the process exerts a profound influence upon the yield of the endproducts in the aminomethylation reaction. On using strongly basic amines, however, a portion is lost not only in transiently absorbing the carbon dioxide formed, but also by reaction with carbon monoxide to the corresponding formamides. I have now found that for the best catalytic effect, a minimum basicity requirement of the reaction medium has to be fulfilled. This is achieved, in accordance with the present invention, by replacing a part of excess amine to be reacted with a strongly basic tertiary amine, which is liquid at the reaction temperature. The loss of the amine reactant can thus be avoided or greatly reduced and the tertiary amine, acting as a solvent and remaining unattached during the reaction, may be recovered and recycled. The use of the tertiary amine also permits the aminomethylation reaction with less basic amines.

The term "olefin" as herein used means any organic compound having at least one ethylenic unsaturation capable of undergoing aminomethylation. Olefins which are suited for the process are known to the art.

The expression "strongly basic teritary amine" includes any inert tertiary amine having a dissociation constant in aqueous solution of at least $pK_a = 10$ such as, for example, triethyl amine, N,N-dimethylbutylamine, N-methylpyrrolidine, N,N-dimethylpiperazine, N-ethylpiperidine, tetraethylurea, pentamethylguandine and the like.

Suitable starting amines having at least one reactive nitrogen-hydrogen bond able to undergo the aminomethylation reaction are known to the art.

The term "catalyst" used in connection with the presented iron carbonyl and rhodium oxide is intended to include any modification which the original catalyst or catalyst combination will pass through in the reaction environment. Therefore, denoting herein iron carbonyl as synergistic or co-catalyst and rhodium oxide as catalyst, signifies that catalytic aminomethylation of olefins can be performed in simpler manner by using these starting metal compounds rather than the true catalytic species which may be formed in the presence of olefin, amine, carbon monoxide and water. Those skilled in the art will understand that the possibly modified catalyst could also be isolated from the reaction mixture by methods known in metal complex chemistry and be used as well. However, the catalyst formation "in situ" is more convenient and preferred. I have found that any rhodium compound which can be converted to the carbonyl or carbonyl hydride under the reaction conditions, can also be used instead of the oxide. The catalyst is employed in catalytically effective amounts.

Numerous improvements known to the art for carrying out catalytic aminomethylations using olefins, amines, carbon monoxide and water may be employed if desired in the present invention. This improved method is also applicable to the aminomethylations, where hydrogen has been used instead of water.

The amines which are obtained in accordance with the present invention are highly valuable per se. The amines having a $C_8$ and $C_{18}$ alkyl find application in the detergent field. Other utilities of primary, secondary and tertiary amines are known to the art.

Thus, the present invention broadly contemplates the aminomethylation of olefins to produce primary, secondary and tertiary amines. In its more limited scope, the method is applied to the aminomethylation of alicyclic, (up to 10 C atoms), and $C_4$ to $C_{24}$ alkyl olefins, especially $C_8$ to $C_{18}$ alkyl olefins, which method is characterized by its simplicity, versatility and use of a relatively small amount of catalyst combinations to obtain tertiary amines in yields of 90%, calculated on the olefin originally employed. No decomposition of the catalyst to inactive species takes place during the reaction, the shorter reaction periods lead to higher yields of desired endproducts.

The present invention provides an improved process for producing primary, secondary and tertiary amines from a wide range of aliphatic and alicyclic olefins.

In order to illustrate the widely differing catalytic properties of iron pentacarbonyl and rhodium oxide and combination thereof, some characteristic results obtained with cyclohexene, dodecenes, and tetradecenes, and with pyrrolidine and dimethylamine, have been selected among numerous experiments carried out with olefins and amines. These results are compiled in the Table 1–3.

The aminomethylation was carried out in a 0.5 liter stainless steel rocking autoclave containing the reaction mixture consisting of 0.25 mol olefin, 0.5 mol secondary amine, 0.5 mol water, the indicated amount of catalyst and possibly 60 ml N-methylpyrrolidine. The mixture was heated under an initial carbon monoxide pressure of 140 atmospheres at 170°C for 3 hours. The various products formed were identified by micro analysis and, where possible, by gaschromatographic and spectroscopic comparison with authentic samples. In some instances, the amines were also determined by non-aqueous titration.

TABLE I

CATALYTIC AMINOMETHYLATION OF OLEFINS

| Olefin | Sec. Amine | Aminomethylation Product | Yield[% calc'd on olefin] of aminomethylation products in the presence of | | |
|---|---|---|---|---|---|
| | | | Fe(CO) 0.025 mol | $Rh_2O_3$ 0.0005 mol | $Fe(CO)_5+Rh_2O_3$ |
| Cyclohexene | Pyrrolidine | 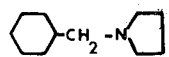 | 6.0[a] | 80.0[b] | 93.5[a] |
| Cyclohexene | Dimethylamine | 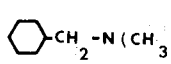 | Traces[a] | 51.0[c] | 91.0[a] |
| Dodecenes | Dimethylamine | N.N-Dimethylaminomethyldodecanes | 1.8 | 50.0[d] | 90.0 |
| Tetradecenes | Dimethylamine | N.N-Dimethylamino- | 1.5 | 55.0[d] | 92.0 |

TABLE I-continued

CATALYTIC AMINOMETHYLATION OF OLEFINS

| Olefin | Sec. Amine | Aminomethylation Product | Yield[% calc'd on olefin] of aminomethylation products in the presence of | | |
|---|---|---|---|---|---|
| | | | $Fe(CO)_5$ 0.025 mol | $Rh_2O_3$ 0.0005 mol | $Fe(CO)_5+Rh_2O_3$ |
| | | methyltetradecanes | | | | inclusive
"1–2% of hexahydrobenzyl alcohol
$^b$6–11% of N-hexahydrobenzoyl pyrrolidine and 3–4% of hexahydrobenzyl alcohol
$^c$5–9% of N-hexahydrobenzoyl dimethylamine and 4–5% of oxo products
$^d$4–8% of oxo products

TABLE 2

AMINOMETHYLATION OF TETRADECENES IN THE PRESENCE OF RHODIUM OXIDE AND VARYING QUANTITIES OF $Fe(CO)_5$.

| Catalyst Concn. (mol%, calculated on olefin) | | N.N-dimethylaminomethyltetradecanes (% yield, calculated on olefin) |
|---|---|---|
| $Rh_2O_3$ | $Fe(CO)_5$ | |
| 0.2 | 10 | 92.0 |
| 0.2 | 5 | 90.8 |
| 0.2 | 2 | 89.0 |
| 0.2 | 1 | 88.0 |
| 0.2 | 0 | 55.0 |

TABLE 3

EFFECT OF THE AMINE CONCENTRATION IN THE AMINOMETHYLATION OF OLEFINS
(AMINE = PYRROLIDINE; OLEFIN = CYCLOHEXENE, CATALYST = Rh/Fe COMBINATION)

| Pyrrolidine Concen. (mol % based on olefin) | ⌬–CH$_2$–N⌬ | ⌬–CH$_2$OH | Residue (g) |
|---|---|---|---|
| | (Yield, % calc'd on olefin) | | |
| 100 | 46.5 | 1.0 | 3 |
| 125 | 60.0 | <1 | 3 |
| 150 | 78.0 | 1 | 1.5 |
| 200 | 90.0 | 1.0 | 0.5 |
| 100* | 71.0 | 3.5 | 3.2 |
| 125* | 88.0 | 1.6 | 1.2 |

$Rh_2O_3$ = 0.0005 mol
$Fe(CO)_5$ = 0.0125 mol
*100 mol % (based on olefin) of N-Methylpyrrolidine used additionally as solvent in these experiments.

As can be seen from Table I, iron pentacarbonyl affords poor yields of the desired tertiary amines from both, aliphatic and alicyclic olefins. The yields are lying in the range of from 1 to 6%, based upon the olefin.

On the whole, much more improved results are obtained by replacing the iron pentacarbonyl by rhodium oxide. Fairly high yields of tertiary amines, ranging from 50 to 80%, based on olefin, are obtained. The olefin conversions are lying, on average, between 60 and 90%. However, in contrast to the iron pentacarbonyl catalyzed reaction, when working with rhodium oxide, competing reactions leads to considerable formation of by products, such as carboxamides and hydroxymethyl derivatives. Thus, iron carbonyl gave no N-hexahydrobenzoylpyrrolidine from cyclohexene and pyrrolidine, whereas as high as 11% of carboxamide, based on feed cyclohexene, is formed in the presence of rhodium oxide. I have found that the extent of the carboxamide formation in the rhodium catalyzed synthesis is dependent upon the nature of the reaction components and parameters employed.

It is further evident from Table 1, that iron pentacarbonyl in conjunction with rhodium oxide not only suppressed the undesirable side reactions mentioned above, but also raised the yield of the aminomethylated products to over 90%. In the majority of the cases, the addition of iron pentacarbonyl to rhodium oxide raised the yields of the aminomethylated products to over 90%. In the majority of the cases, the addition of iron pentacarbonyl to rhodium oxide raised the yields of the endproducts by approximately 35–40%. It is further apparent that heterocyclic amines are particularly suited to the rhodium catalyzed aminomethylation of olefins.

As also conspicuously illustrated by the results compiled in Table 2, iron pentacarbonyl concentrations as low as 1 to 2 mol %, based on olefin, can be employed with success as co-catalyst. This reduces to a great extent the hazards involved in handling large amounts of toxic iron pentacarbonyl.

I further found that strongly basic amines react best in the aminomethylation and that loss of amine reactant through carbonate and formamide formation can be avoided, when a strongly basic tertiary amine is substituted for a part of the excess amine reactant, as is obvious from Table 3, on comparing the first two runs with the last two runs.

EXAMPLE 1

Aminomethylation of cyclohexene, using pyrrolidine

A stainless steel rocking autoclave was charged with the required amounts of cyclohexene, pyrrolidine, N-methylpyrrolidine (Fluka, pract.), and water and pressurized by carbon monoxide to 140 atm. It was then heated to 170°C (approximately 45 minutes) and the contents of the autoclave shaken at this temperature for another 2 hours. On completion of the reaction period the pressure vessel was cooled and the gases vented. The reaction mixture was removed and scrubbed with water, in order to remove the unreacted secondary amines, correspondingly their N-formyl derivatives (formed in a side reaction), and the N-methylpyrrolidine solvent, all of which are water-soluble. The aqueous phase was extracted once with pentane. The organic phase, together with the pentane extract were dried over sodium sulfate and fractionally distilled.

Beside the starting olefin, with rhodium oxide catalyst two fractions (b.p. 86°–90°C/11 torr and 140°–145°C/10 torr respectively) were obtained with iron carbonyl or iron carbonyl/rhodium oxide combination only the lower boiling fraction (b.p. 86°–90°c/11 torr) were obtained. The fraction boiling between 86°–90°C/11 torr was shown by gaschromatographic and i.r. spectroscopic comparisons with authentic samples to contain hydroxymethylcyclohexane and N-hexahydrobenzylpyrrolidine. Amine yields are determined by non-aqueous titration with perchloric acid, as well as by separating the tertiary amines as hydrochlorides and recovering the free base by treatment with sodium hydroxide.

| ⌬-CH₂-N⌬ | b.p. 89–90°C/11 torr | | | |
|---|---|---|---|---|
| | C | H | N | Mol. Wt. |
| Calc'd ($C_{11}H_{21}N$) | 78.90 | 12.65 | 8.37 | 167.3 |
| Found | 78.09 | 12.65 | 8.50 | 170 |

The higher boiling fraction, which solidified in the cooler, was identified as N-hexahydrobenzolypyrrolidine by micro analysis, as well as by mixed melting point measurement and spectroscopic comparison with an authentic sample.

| ⌬-C(=O)-N⌬ | b.p. 140–145°C/10 torr | | | |
|---|---|---|---|---|
| | m.p. 71°C (from hexane) | | | |
| | C | H | N | Mol. Wt. |
| Calc'd ($C_{11}H_{19}ON$) | 72.88 | 10.56 | 7.73 | 181.3 |
| Found | 73.48 | 10.62 | 7.54 | 188 |

EXAMPLE 2

Aminomethylation of cyclohexene using dimethylamine

The reaction of cyclohexene with dimethylamine in the presence of carbon monoxide and water and the subsequent processing of the resulting products were carried out following the general procedures of Example 1. Likewise, depending on the nature of the catalyst employed, either one or two product fractions were obtained on distillation. The lower boiling fraction consisted of N.N-dimethylaminomethyl cyclohexane, its identity being confirmed by micro analysis, gaschromatographic and spectroscopic comparison with an authentic sample.

| ⌬-CH₂-N(CH₃)₂ | b.p. 55–56°C/11 torr | | |
|---|---|---|---|
| | C | H | N |
| Calc'd ($C_9H_{19}N$) | 76.53 | 13.56 | 9.92 |
| Found | 76.65 | 13.49 | 10.09 |

The higher boiling fraction (88°–118°C/11 torr) also obtained particularly when working with rhodium oxide, was analyzed gaschromatographically and found to be composed of formyl-, as well as hydroxymethyl- and N.N-dimethylcarbamoylcyclohexane [$C_6H_{11}CON(CH_3)_2$].

EXAMPLE 3

Aminomethylation of n-dodecenes and n-tetradecenes by dimethylamine

These reactions were preformed in the general manner of the previous examples. The mixtures resulting from n-dodecenes or n-tetradecenes were distilled and the fractions boiling between 90°–140°C/10 torr, correspondingly 90°–140°C/4 torr were collected. As previously mentioned, the amounts of the aminomethylated products in these fractions were determined either by separation of the tertiary amines as hydrochloride and recovery by treatment with alkali, or via titration with perchloric acid.

| X- N.N-Dimethylaminomethyl-dodecane [X = 1–6] | b.p. 120–140°C/10 torr | | | |
|---|---|---|---|---|
| | C | H | N | Mol. Wt. |
| Calc'd ($C_{15}H_{33}N$) | 79.21 | 14.62 | 6.16 | 227 |
| Found | 79.83 | 14.81 | 5.48 | 234 |

EXAMPLE 4

A solution of cyclohexane (0.25 mole), piperidine (0.5 mole), water (0.5 mole) and $Fe(CO)_5$ (0.025 mole) in 60 ml N-methylpyrrolidine and rhodium hydroxide [$Rh(OH)_3$] ($5\times10^{-3}$ mole) were charged into a stainless steel rocking autoclave of 0.5 liter capacity. The reaction chamber was pressurized by carbon monoxide at 140 atm and heated at 170° for 3 hours. On completion of the reaction period, the pressure vessel was allowed to cool and the gases vented. The reaction mixture was taken out and scrubbed 2–3 times with water in order to remove the unreacted secondary amine, its N-formyl derivative (formed in a side reaction), and the solvent, all of which are water-soluble. The aqueous phase was extracted once with pentane. The organic phase and the pentane extract were combined and dried over sodium sulfate and fractionally distilled to yield N-hexahydrobenzylpiperidine (ca. 80% yield), the product being unequivocally identified by gas-liquid chromatographic and spectroscopic (ir, nmr) comparison with an authentic sample.

EXAMPLE 5

In place of rhodium hydroxide of Example 4, there was used rhodium acetate [$Rh(OAc)_2$]$_2$ as catalyst.

The yield of N-hexahydrobenzylpiperidine was ca. 85%.

EXAMPLE 6

By using $Rh_6(CO)_{16}$ as catalyst, 1.2-bis-(dimethylamino)-ethane as solvent, pyrrolidine as amine component, and otherwise following the procedure of Example 4 ca. 80% conversion of cyclohexene to N-hexahydrobenzylpyrrolidine was obtained.

EXAMPLE 7

In place of rhodium hydroxide of Example 4 there was used $ClRh(PPh_3)_3$ as catalyst. A conversion of ca. 80% of cyclohexene to N-hexahydrobenzylpiperidine was obtained.

EXAMPLE 8

By a procedure similar to that of Example 4, using $Rh_4(CO)_{12}$ and dimethyl amine under somewhat milder conditions (140°C, 100 atm) norbornene was converted to exo-3-dimethylaminomethyl-bicyclo-[2.2.1]-heptane (ca. 30% yield).

EXAMPLE 9

A 0.5 l stainless steel rocking autoclave was charged with cyclohexene (0.1 mole), ammonium formate (0.2 mole), water (0.1 mole), $Rh_6(CO)_{16}$ ($5\times10^{-4}$ mole), $Fe(CO)_5$ (0.5 ml), pyridine (50 ml) and pressurized by carbon monoxide to 75 atm. It was then heated to 160°C — this required in general ca. 35 minutes — and the contents of the autoclave shaken at said temperatures for 12 hours. On completion of the reaction period the pressure vessel was cooled and the gases vented. The reaction mixture was filtered to yield 5.6 g of a white crystalline compound (m.p. 89°–90°C). On removal of solvent from the filtrate there was obtained a second crop of crystals (0.4 g, m.p. 86°–89°C). The two solid products (total yield ca. 60%) were found to be identical and unequivocally characterized as tris-(cyclohexylmethyl)-amine (ir, nmr).

EXAMPLE 10

By the procedure of Example 9, however in the absence of water, only ca. 40% of tris-(cyclohexylmethyl)-amine was obtained. At the same time considerable amounts of N-(cyclohexylmethyl)-formamide and N.N.-di(cyclohexylmethyl)-formamide were formed.

EXAMPLE 11

In place of ammonium formate of Example 7, there was used an equivalent amount of gaseous ammonia. A total conversion of ca. 80% of cyclohexene was obtained. The mixture of products mainly consisted of tris-(cyclohexylmethyl)-amine and the N-formyl derivatives of aminomethylcyclohexene and N.N-di(cyclohexylmethyl)amine.

EXAMPLE 12

A solution of n-octene-1(0.05 mole), dimethylamine (10 ml), water (0.1 mole), iron pentacarbonyl (0.5 ml) and $RhCl_3.3H_2O$ ($5\times10^{-4}$ mole) in 25 ml triethylamine was charged into a stainless steel rocking autoclave of 0.5 l capacity. The autoclave was pressurized by carbon monoxide to 100 atm and heated at 140°C for 8 hours. On completion of the reaction period, the pressure vessel was allowed to cool and the reaction gases were vented. The reaction mixture was removed and scrubbed 2-3 times with water in order to eliminate the unreacted secondary amine, its N-formyl derivative (formed in a side reaction) and the solvent. The aqueous phase was extracted once with pentane. The organic phase, together with the pentane extract were dried over sodium sulfate and fractionally distilled to yield all the four possible (N.N-dimethylaminomethyl)-octanes (ca. 85% yield based on olefin) with the following approximate isomeric distribution (gas-liquid chromatography):

| | |
|---|---|
| $CH_3CH_2CH_2CH_2CH_2CH_2CH_2CH_2-N(CH_3)_2$ | 65% |
| $CH_3CH_2CH_2CH_2CH_2CH_2CHCH_3$<br>                                                          $N(CH_3)_2$ | 30% |
| $CH_3CH_2CH_2CH_2CH_2 \; CHCH_2CH_3$<br>                                                    $N(CH_3)_2$ | 3.3% |
| $CH_3CH_2CH_2CH_2CHCH_2CH_2CH_3$<br>                                      $N(CH_3)_2$ | 1.7% |

EXAMPLE 13

In place of $RhCl_3.3H_2O$ of Example 12 there was used $[Rh(CO)_2Cl]_2$. A ca. 80% conversion of n-octene-1 to the four isomeric N.N.-dimethylaminomethyl)-octanes was obtained.

EXAMPLE 14

In place of $RhCl_3.3H_2O$ of Example 12 there was used $Rh_4(CO)_{12}$. The yield of (N.N-dimethylaminomethyl)-octanes amounted to ca. 85%.

EXAMPLE 15

The findings of Example 12 were essentially unaltered on substituting N-methylpiperidine for triethylamine as solvent.

EXAMPLE 16

In place of piperidine of Example 4, there was used aminomethylcyclohexane. Work up of the mixture according to the procedure outlined in Example 9 yielded ca. 70% of tris-(cyclohexylmethyl)amine, besides small amounts of the formyl derivative of N.N-di(cyclohexylmethyl)-amine.

EXAMPLE 17

In place of n-octene-1 and dimethylamine of Example 12 there were used ethylene and cyclohexylamine, respectively. The major product formed consisted of cyclohexyl-di-n-propylamine (ca. 70%), besides the N-formyl derivative of propylcyclohexylamine.

EXAMPLE 18

In place of piperidine of Example 4, there was used methylamine as the amine reactant. Ca. 70% of cyclohexene was converted to methyl-di-(cyclohexylmethyl)-amine. N-formyl derivative of N-(cyclohexylmethyl)-methylamine was also isolated as a further product.

I claim:
1. In an improved process for the preparation of amine by the catalytic reaction of (1) a nitrogen compound selected from the group consisting of ammonia, ammonium formate, N-methylprrolidine, pyrrolidine, methylamine, dimethylamine, piperidine, N-methylpiperidine, aminomethylcyclohexane, cyclohexylamine, and pyridine, (2) olefin selected from the group consisting of ethylene, cyclohexene, octene dodecene, norbornene and tetradecene, (3) carbon monoxide and (4) water, the improvement which comprises the step of effecting the reaction in the presence of iron pentacarbonyl and a rhodium compound selected from the group consisting of rhodium oxide, rhodium hydroxide, rhodium acetate, rhodium carbonyl, rhodium chloride, tris(triphenylphosphine)rhodium chloride, and rhodium carbonyl chloride, the iron pentacarbonyl being present at 0.5-5 mol % based on the olefin, and the ratio of iron pentacarbonyl to rhodium compound being from 10:1 to 100:1.

2. The process of claim 1 in which the reaction is conducted in the presence of a strongly basic tertiary amine having a dissociation constant in aqueous solution of at least $pK_a = 10$, and being liquid under the reaction condition.

3. The process of claim 1 in which said olefin is an aliphatic olefin having 4 to 24 carbon atoms.

4. The process of claim 1 in which said olefin is an alicyclic olefin having up to 10 carbon atoms.

5. In an improved process for the preparation of N-hexahydrobenzylpyrrolidine by the catalytic reaction of (1) pyrrolidine, (2) cyclohexene, (3) carbon monoxide and (4) water, the improvement which comprises the step of effecting the reaction in the presence of iron pentacarbonyl and rhodium oxide, the molar ratio of iron carbonyl to rhodium oxide being in the range of from about 10:1 to about 100:1.

* * * * *